(12) United States Patent
Miyasaka

(10) Patent No.: US 7,637,858 B2
(45) Date of Patent: Dec. 29, 2009

(54) FUNCTIONAL SHEET

(75) Inventor: Yoshio Miyasaka, Nagoya (JP)

(73) Assignee: Fuji Kihan Co., Ltd., Aichi (JP)

( * ) Notice: Subject to any disclaimer, the term of this patent is extended or adjusted under 35 U.S.C. 154(b) by 22 days.

(21) Appl. No.: 11/578,916

(22) PCT Filed: Apr. 13, 2005

(86) PCT No.: PCT/JP2005/007175

§ 371 (c)(1),
(2), (4) Date: Oct. 18, 2006

(87) PCT Pub. No.: WO2005/102454

PCT Pub. Date: Nov. 3, 2005

(65) Prior Publication Data

US 2007/0219087 A1    Sep. 20, 2007

(30) Foreign Application Priority Data

Apr. 22, 2004    (JP) ............... 2004-127187

(51) Int. Cl.
*A61N 5/00* (2006.01)
(52) U.S. Cl. .................. 600/2; 501/123
(58) Field of Classification Search ......... 600/2; 502/300, 350; 526/341, 869; 501/123; 313/506; 430/319, 321
See application file for complete search history.

(56) References Cited

U.S. PATENT DOCUMENTS 6,949,328 B2 * 9/2005 Ito et al. ............... 430/321
7,151,067 B2 * 12/2006 Sakon et al. ............ 501/123
7,169,733 B2 * 1/2007 Wang et al. ............ 502/300

FOREIGN PATENT DOCUMENTS

| JP | 55-67727 | | 5/1980 |
| JP | 11-333298 | | 7/1999 |
| JP | 2000167397 | A * | 6/2000 |
| JP | 2001-187155 | | 7/2001 |
| JP | 2001-254031 | | 9/2001 |
| JP | 2002-004023 | | 9/2002 |

* cited by examiner

*Primary Examiner*—John P Lacyk
(74) *Attorney, Agent, or Firm*—Porzio, Bromberg & Newman, P.C.

(57) ABSTRACT

A functional sheet which exercises desired actions such as healing effect in high efficiency, without restriction by its use condition and the like is provided. A functional sheet 1 which exercises functions such as healing effect, relaxation effect, decomposition and removal of harmful substances according to complex functions such as generation of minus ions and/or photocatalyst function, by supporting a photocatalyst powder 10 such as titania ($TiO_2$), tin oxide (SnO), zinc oxide (ZnO), $SnO_2$, $ZrO_2$, and $WO_3$ which is oxidized in a structure of which a bond with oxygen is decreased as goes from its surface into the inside gradually, and a radioactive powder 20 containing a natural radioactive substance such as thorium (Th), for example, the powder of monazite, in a condition in which they are mutually brought in contact or adjacent, on a carrier 30 which forms a sheet shape composed by entangling a lot of fibers such as nonwoven fabric.

5 Claims, 2 Drawing Sheets

FUNCTIONAL SHEET

BACKGROUND OF THE INVENTION

1. Field of the Invention

The present invention relates to a sheet to which various desired functions such as the discharge of radiation ray at a comparatively low level and the action of photocatalyst are added. In the present specification, a sheet to which a desired function is added thus is called as a "functional sheet". Additionally, the representation of "functional ---" means that a desired function is imparted to an "article" which a terminology of the second element inserted in the portion of "---" indicates. More specifically, the present invention relates to a functional sheet which can be used for obtaining, for example, health-promoting effect, relaxation effect, antibacterial and deodorization effects, and the like, which are obtained by irradiation of radiation ray at a comparatively low level, by generation of minus ions, and the like.

2. Description of the Prior Art

Various functional fiber products in which a desired function is imparted to a fiber product (for example, a cloth) have been conventionally developed. As one example, there exist a functional fiber product, in which far infrared ceramics generating far infrared rays, tourmaline generating minus ions, and the like are finely pulverized to be kneaded in fiber materials such as a nylon and a polyester or to be supported by nonwoven fabrics, in order to add functions such as the promotion of blood circulation by far infrared rays, improvement of immunizing power by generation of minus ions, and other health-promoting effects, removal of a harmful substance, and deodorization. Alternatively, there exists a functional fiber product in which the powder of an adsorptive substance such as zeolite and bincho charcoal is dispersed in nonwoven fabric for purpose such as removal of a harmful substance, deodorization, and the like, by adsorptive action. The functional fiber products having various functionality, thus obtained are used as clothes, bedclothes, accessories, various filters, and the like.

As an example, in "Product development with minus ion fibers," The Senken Shimbun, Jun. 12, 2001 discloses a fiber product, in order to obtain relaxation effect and/or improve vital function, in which bincho charcoal, specific ceramics, tourmaline, and the like are kneaded in raw material for a synthetic fiber. Alternatively, a fiber product using raw thread obtained by finely pulverizing a mixture of natural ores such as granitoid or schiller rock containing rare-earth elements, and by kneading the pulverized mixture in polyester or raw material for rayon.

Although various functions are added in these functional fiber products in accordance with property of powder component kneaded or supported in the fiber, any of these functional fiber products is inferior in its efficiency.

For example, in case of a fiber product for adding function of adsorbing a harmful substance and/or an odor component, and the like by supporting a porous substance such as bincho charcoal or zeolite among the fore-description, since the porous substance such as bincho charcoal and zeolite is an "adsorptive substance" which catches and removes a harmful substance and/or an odor component, and the like in pores, the fiber product does not carry out adsorption once the product catches a harmful substance and/or an odor component and the like in pores.

Further, among the fore-description, far infrared ceramics is added or supported with a purpose of, by generating far infrared rays and irradiating the rays, for example, to human body, thus adding functions such as the improvement of stiff neck or feeling of cold by promoting blood circulation, but the far infrared ceramics generates only trace amount of infrared rays under a condition in which thermal energy is not added to the far infrared ceramics, therefore the effect has limitation. Accordingly, if the far infrared ceramics is used alone, little effect is expected.

Further, tourmaline, which is called as an electric stone, generates minus ions and thereby, is added or supported with a purpose of adding function of relaxation effect and/or improvement of vital function, and the like, but vibration is required for generating minus ions.

Thus, the functional fiber products, in which the fore-mentioned substances are kneaded or supported, requires to be used under an environment satisfying a certain condition for obtaining a desired effect, but any of the fore-mentioned functional fiber products is inferior in efficiency, and high effect cannot be obtained.

On the other hand, a functional fiber product, in which powder of ores (for example, monazite and the like) containing a radioactive rare-earth element such as thorium (Th) is kneaded in a fiber material of a synthetic fiber product to generate radiation ray, is also developed, and the functional fiber product can radiate radiation ray without addition of energy from the outside.

However, the treatment of such radioactive substance must be generally out of the application range of the Radiation Hazards Prevention Law which is a safety standard in Japan (a case that concentration and quantity are comparatively little), and there is limitation for concentration and the like at which the radioactive substance can be supported to the functional fiber product and the like (as an example, the concentration in a solid is 370 Bq/g or less). Accordingly, there is also limit for effect obtained by the functional fiber product.

On the other hand, when the concentration, quantity, and the like of the radioactive substance supported in the fiber product is much, there is a fear that radiation hazard is generated.

Further, the fore-mentioned functional fiber product, in which forecited monazite and the like are kneaded in a fiber material, requires that ores such as monazite is finely pulverized to a level at which the ores can be kneaded in the fiber material of a synthetic fiber, and there are problems that production cost is high and that life time is comparatively short.

Further, in addition to the fore-described ores, a photocatalyst substance such as titanium oxide is known, and there is also developed a functional fiber product which has functions of generating minus ions and decomposing harmful substances, and the like by supporting the powder of the photocatalyst substance in a fiber product.

However, a general photocatalyst substance is called as "anatase type", and exercises photocatalyst function of generating minus ions and decomposing harmful substances, and the like in reaction with an ultraviolet component among light when the photocatalyst substance is irradiated by light, and since the photocatalyst substance hardly react with light in the visible light region, the fore-mentioned action is not exercised in room or dark place. Accordingly, the use of the functional fiber product is limited.

To the contrary, in Japanese Patent KOKAI (LOPI) No. 2002-85981 (hereinafter, referred to as "prior art"), as a photocatalyst substance exercising photocatalyst function in response not only to ultraviolet rays but also to electromagnetic wave with a longer wavelength than ultraviolet rays (γ-ray, X-ray, lights such as ultraviolet rays, visible light and infrared rays, and electric wave), there is also developed a photocatalyst substance described later in detail formed by a metal coating which has a tilting structure (in the present specification, called as the "oxygen deficit tilting structure"), of which oxygen to be bonded is decreased as goes from a surface to the inside gradually, on the surface of a treated product comprising a metal, ceramics or a mixture thereof.

In functional fiber product which are composed as above, for example, when clothe, for example, an underwear and the like, is produced from functional fiber products supporting powders, such as bincho charcoal, far infrared ceramics, and tourmaline, which require external addition of heat and vibration energy for the generation of far infrared rays or generation of minus ions, and when a person wears the clothe for the promotion of blood circulation of the human body, these functional fiber products can utilize only limited energy such as body heat and cannot adequately make use of the effect, since these functional fiber products are used in a condition in which they are shielded from the outside by outer wears and the like which are worn over the functional fiber product.

Since the photocatalyst substance, equipped with an oxide coating film having the oxygen deficit tilting structure shown in the prior art, exercises a photocatalyst function in response to electromagnetic wave with a longer wave length than ultraviolet rays, the photocatalyst reaction can be generated by receiving the irradiation of electromagnetic wave which passes outer wears, even if the product is used in a condition in which the product is shielded from the outside by outer wears and the like, but the reaction is not also occasionally carried out adequately in this case.

Further, since in the photocatalyst substance described in the prior art, for example, an oxide coating film is formed on the surface of a treated product by injecting a metal powder being the oxide coating film on the surface of the treated product by a blast method and the like. Thereby, the shape and size of the photocatalyst substance produced is limited by the shape or size of the treated product. Further, since it is difficult for a minute object such as powder to be used as a treated product and to form an oxide coating film on the minute object, the photocatalyst substance obtained is a comparatively large size.

As a result, as mentioned above, it is difficult to obtain a photocatalyst with a powder size which can be supported in a functional fiber product, and it is difficult to enlarge a specific surface.

On the other hand, the functional fiber product, in which the powder of ores containing a radioactive substance such as monazite that contains a rare-earth element such as thorium (Th), for example, is supported, can radiate radiation ray without input of energy from the outside, but as mentioned above, since there is a limit for the amount of powder which can be supported, the product cannot exercise various functions in high efficiency.

Accordingly, the present invention is achieved for solving defects in the above-mentioned conventional technology, and it is the purpose of the present invention to provide a functional fiber product which can make powder supported exercise desired functions in high efficiency without input of energy from the outside, and which is hardly subject to limitation by use condition and the like of the product.

SUMMARY OF THE INVENTION

In order to achieve the above-mentioned purposes, a functional sheet 1 of the present invention is characterized in being equipped with, a photocatalyst powder 10 in which a metal powder exercising a photocatalyst function by oxidation is oxidized in a structure of which a bond with oxygen is decreased as goes from the surface of the powder to the inside gradually, a radioactive powder 20 containing a natural radioactive substance, and a carrier 30, such as nonwoven fabric or paper, which forms a sheet shape composed by entangling a lot of fibers and which supports the photocatalyst powder 10 and the radioactive powder 20 in a condition in which the powders are mutually brought in contact or adjacent (claim 1).

In the functional sheet 1 of the above-mentioned composition, as the photocatalyst powder 10, powder can be used which is prepared by injecting and bombarding a metal powder such as, for example, titanium (Ti), tin (Sn), zinc (Zn), zirconium (Zr), and tungsten (W), that exercises a photocatalyst function by oxidation, on an object to be bombarded comprising a metal, ceramics, or a mixture thereof, that has a melting point equal or more to the melting point of the metal powder, together with compressed gas, thereby oxidizing the metal powder (claim 2).

Further, the carrier 30 is set as a laminated structure and may be a composition in which the carrier supports the photocatalyst powder 10 and the radioactive powder 20 by placing them between the layers (31, 32) of the carrier 30 in a mixed condition (claim 3; refer to FIG. 1). Alternatively, the carrier 30 may be a composition in which the carrier 30 has a laminated structure of 3 layers or more and supports the photocatalyst powder 10 and the radioactive powder 20 by placing the powders of photocatalyst and radioactivation respectively between the layers of the carrier 30 individually (claim 4; refer to FIGS. 2 and 3).

Further, preferably, the particle diameters of the photocatalyst powder 10 and the radioactive powder 20 have a particle diameter of from # 46 (420 μm) to # 220 (44 μm) (claim 5).

The range of the above-mentioned particle diameter is both applied to the particle diameters of the photocatalyst powder and the radioactive powder, and a portion (specific surface) generating a photocatalyst reaction can be increased by setting the particle diameter, with respect to the photocatalyst substance, to a comparatively small diameter. Further, when the particle diameter is # 46 or less, the diameter is not appropriate since when the powder is directly brought in contact with a skin, pain is generated, and when the particle diameter exceeds # 220, the powder leaks from the texture of nonwoven fabric.

Further, when the natural radioactive substance is thorium (Th), the radioactive powder 20 can be supported on the carrier 30 so that thorium is 0.1 to 2.0 wt % at a weight ratio based on the total weight of the functional sheet 1 obtained (claim 6).

The amount of thorium means 0.1 to 2.0 wt % based on the total weight (the weight of the carrier (nonwoven fabrics)+the weight of the photocatalyst powder+the weight of the radioactive powder) of the "functional sheet" prepared as the above-description, whereby, as mentioned later, the concentration of the radioactive substance in the functional sheet 1 obtained can be suppressed to 370 Bq/g of solid or less which is within a range of regulations in Japan.

According to the composition of the present invention illustrated above, remarkable points the functional sheet 1 of the present invention are as follows:—

(1) A functional sheet 1 to which the function of irradiation of radiation ray and the photocatalyst function are simultaneously added can be provided by supporting a photocatalyst powder 10 having the oxygen deficit tilting structure together with a radioactive powder 20 on a carrier 30.

Then, since the photocatalyst powder 10 responds to electromagnetic wave with a longer wave length than ultraviolet rays to exercise the photocatalyst function, the photocatalyst reaction occurs in response to radiation ray which is radiated from the radioactive powder 20, and an adequate photocatalyst reaction can be generated even if the product is used under use environment at which the input of energy from the outside is limited. Additionally, desired effects could be obtained with high efficiency by supplementing the action of the radioactive powder 20 by the photocatalyst reaction, even if a small amount of the radioactive powder 20 having no danger of radiation hazard is supported.

(2) The photocatalyst powder 10 which responds to electromagnetic wave with a longer wave length than ultraviolet rays can be comparatively easily obtained by bombarding a metal powder injected together with compressed air, on an object to be bombarded and oxidizing the metal powder in the oxygen deficit tilting structure.

(3) When the carrier 30 is composed as a laminated structure; and when the photocatalyst powder 10 and the radioactive powder 20 are supported on the carrier 30 by placing the photocatalyst powder 10 and the radioactive powder 20 in a mixed condition or individually between the layers of the carrier 30, the functional sheet 1 with a simple structure which can be easily produced can be provided.

(4) Further, the specific surface of the photocatalyst powder 10 can be enlarged and the photocatalyst reaction can be easily generated, by forming the particle diameters of the photocatalyst powder 10 and the radioactive powder 20 in a comparatively small particle diameter of from # 46 (420 µm) to # 220 (44 µm).

(5) Further, the dose of radiation ray can be out of the application range (concentration in a solid is 370 Bq/g or less) of the Radiation Hazards Prevention Law, by setting thorium as the natural radioactive substance and the content of thorium to 0.1 to 2.0 wt % at a weight ratio based on the total weight of the functional sheet.

BRIEF DESCRIPTION OF THE DRAWINGS

The objects and advantages of the invention will become apparent from the following detailed description of preferred embodiments thereof provided in connection with the accompanying drawings in which.

The objects and advantages of the invention will become apparent from the following detailed description of preferred embodiments thereof provided in connection with the accompanying drawings in which.

DETAILED DESCRIPTION OF PREFERRED EMBODIMENTS

Then, embodiments of the present invention are illustrated below.

(Whole Structure)

A functional sheet 1 of the present invention is equipped with a structure, in which a photocatalyst powder 10, in which a metal powder exercising a photocatalyst function by oxidation is oxidized in the oxygen deficit tilting structure, together with a radioactive powder 20, containing a natural radioactive substance, are supported on a sheet-shaped carrier 30.

The carrier 30 forms a sheet shape which is composed by entangling a lot of fibers, and various articles such as nonwoven fabric or paper can be used, so far as the photocatalyst powder 10 and the radioactive powder 20 cannot pass the article and preferably fibers are entangled to a level at which permeability to air can be secured. Various materials such as natural and synthetic articles can be used without limitation.

The method of supporting the photocatalyst powder 10 and the radioactive powder 20 may be, for example, a method of supporting the powders by entangling the respective powders with fibers composing carriers at a process of producing carriers such as the nonwoven fabric or paper, and various compositions can be adopted so far as the compositions can support the photocatalyst powder 10 and the radioactive powder 20 in a condition in which the powders are mutually brought in contact or adjacent.

In the present embodiment, the carrier 30 has a laminated structure which is formed by overlapping or laminating a plural number of sheets, and by placing the photocatalyst powder 10 and the radioactive powder 20 between the respective layers constituting the carrier 30, the powders are supported. As an example, the carrier 30 is composed as the laminated structure overlapping or laminating a plural number of nonwoven fabrics, and supports both powders in a contact or adjacent condition by placing the photocatalyst powder 10 and the radioactive powder 20 in a mixed condition between the respective nonwoven fabrics constituting the layer of the carrier 30, or by placing respective powders between different layers.

Figure 1:
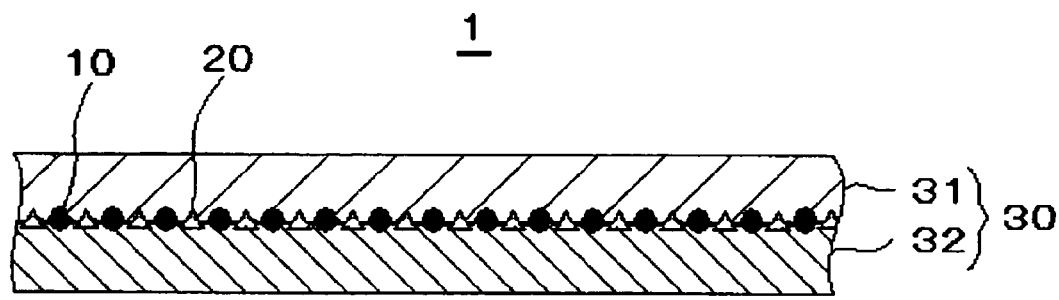
FIG. 1 is a sectional schematic view of a functional sheet showing one embodiment of the present invention.
Figure 2:
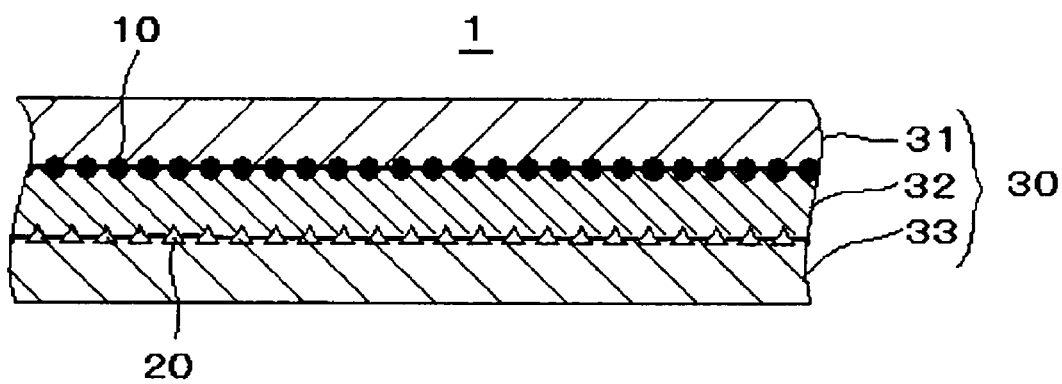
FIG. 2 is a sectional schematic view of a functional sheet showing another embodiment of the present invention.
Figure 3:
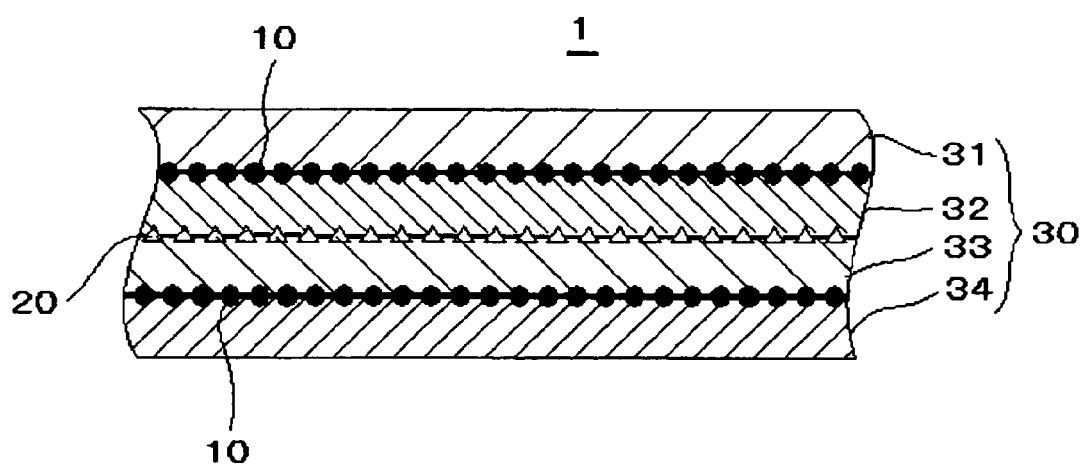
FIG. 3 is a sectional schematic view of the functional sheet showing yet another embodiment of the present invention.

An embodiment shown of FIG. 1 is an example placing the photocatalyst powder 10 and the radioactive powder 20 in a mixed condition between 2 sheets of nonwoven fabrics 31 and 32. An embodiment shown in FIG. 2 is an example in which the carrier 30 comprising the laminated layer of 3 sheets of nonwoven fabrics 31 to 33 is formed, the photocatalyst powder 10 is placed between the first layer 31 and the second layer 32, and the radioactive powder 20 is placed between the second layer 32 and the third layer 33. Further, an embodiment shown in FIG. 3 is an embodiment in which the carrier 30 is formed by the laminated layer of 4 sheets of nonwoven fabrics 31 to 34, the photocatalyst powder 10 is placed between the first layer 31 and the second layer 32 and between the third layer 33 and the fourth layer 34, and the radioactive powder 20 is placed between the second layer 32 and the third layer 33.

(Photocatalyst Powder)

The photocatalyst powder 10, which is supported on the carrier 30, is powder which is supported on the carrier 30 as a photocatalyst substance exercising a photocatalyst function in response to electromagnetic wave with a longer wave length than ultraviolet rays, and uses an oxidized powder having the oxygen deficit tilting structure of which a bond with oxygen is obliquely decreased as goes from the surface to the inside by a method described later.

Example of the metal exercising a photocatalyst function by oxidation can include titanium (Ti), tin (Sn), zinc (Zn), zirconium (Zr), tungsten (W), and the like, and an oxidized structure as the oxidation of the oxygen deficit tilting structure can be formed by injecting and bombarding the various kinds of metal powder having various particle diameters dispersed in a normal distribution on an object to be bombarded comprising a metal, ceramics, or a mixture thereof which has a melting point equal or more to the that of these metal powder, together with compressed gas such as compressed air.

Metal oxides such as titania ($TiO_2$), tin oxide (SnO), zinc oxide (ZnO), further, $SnO_2$, $ZrO_2$, and $WO_3$, which are obtained by oxidizing these metals, have high photocatalyst function.

In the present invention, the photocatalyst is obtained by oxidizing the "powder" of a metal in order to secure a catalyst area widely, and the smaller the particle diameter of the powder used is, the larger the specific surface area is and the higher the catalyst efficiency is. However, the particle diameter of the metal powder is not specifically limited so far as the metal is powder.

In the present invention, since the powder is used by being supported on the carrier 30 which is composed of nonwoven fabric and the like, it is preferable as an example that the particle diameter is from # 46 (420 µm) to # 220 (44 µm).

The shape of the powder is not specifically limited, and any shape such as a sphere may be applied, but a polygonal shape is preferable from the viewpoint of securing the specific surface area widely.

Further, it has been conventionally known, that the catalyst efficiency of a metal oxide such as titania having a photocatalyst function improves when a noble metal such as platinum (Pt), palladium (Pd), gold (Au), or silver (Ag), is supported by 0.1 to 10 wt % based on the photocatalyst powder, and with respect to the photocatalyst powder used in the present invention, these noble metals may be supported on the photocatalyst powder when the photocatalyst powder is obtained by oxidizing the metal powder.

Specifically, the powder of a noble metal such as platinum (Pt), palladium (Pd), gold (Au), or silver (Ag), whose particle diameter is ⅓ or less and preferably ⅒ or less of the metal powder, is mixed with the metal powder comprising metal such as titanium exercising a photocatalyst function by oxidation, and injected. Thereby, the metal powder is not only oxidized by collision to the object to be bombarded, but also collides with the noble metal to support the noble metal.

As the object to be bombarded, a metal, ceramics, or a mixture thereof, which has a melting point equal or more to the metal powder, can be used so that the metal powder is not melted by heat generated at collision, and any shape may be applied so far as collision with the metal powder is obtained and a desired oxidation reaction can be induced for the metal powder by collision with the metal powder injected, and a powder shape in addition to a plate shape may be applied.

When the object to be bombarded is set as a powder shape, a metal powder similar as the metal powder injected can be the object to be bombarded, and in this case, the metal powder is efficiently oxidized while alternatively carrying out the roles of the injecting objective and the object to be bombarded, by injecting the metal powder duplicating on the metal powder injected, and by repeating the works of collection and injecting again.

Known various blast process equipments, and preferably a known air type blast process equipment which injects the metal powder by compressed gas, can be used for the injecting of the metal powder. As an example, the metal powder injected can be oxidized to the fore-mentioned oxygen deficit tilting structure by injecting the metal powders of from # 46 (420 µm) to # 220 (44 µm) at injection speed of 50 m/sec or more and 250 m/sec or less, or at injection pressure of 0.2 MPa or more and 0.7 MPa or less.

It is considered the principle of oxidation in the oxygen deficit tilting structure is generated by collision of the metal powder with the object to be bombarded that when the metal powder is bombarded on the object to be bombarded, the surface of the metal powder is deformed to generate internal friction whereby thermal energy is generated to be heated the metal powder, and the metal powder heated is reacted to be oxidized with oxygen in compressed gas used for injecting or oxygen in air.

The surface side of the metal powder which is exposed to the compressed gas used for injecting or air is easily bound with oxygen, and on the other hand, the metal is hardly bound with oxygen as goes from the surface to the inside. Therefore it is considered that the oxidation of the oxygen deficit tilting structure is generated thereby.

Further, the content of oxygen in the compressed gas used for the injecting of the metal powder may be appropriately adjusted in order to generate the oxidation as preferred.

(Radioactive Powder)

The radioactive powder 20 supported on the carrier 30 together with the fore-mentioned photocatalyst powder 10 can be obtained by pulverizing ores containing radioactive rare-earth elements, for example, can be obtained by pulverizing monazite or ores of rare-earth element, containing thorium (Th) as the rare-earth element.

When the powder containing thorium (Th) is added as the radioactive powder 20, the supported amount of the radioactive powder is adjusted so that the content of thorium in the total weight of the functional sheet produced is 0.1 to 2 wt %.

The reason why the content of thorium (Th) is 2 wt % at maximum is that, when the content of thorium is 2 wt % or less, the concentration of the radioactive substance in the functional sheet 1 obtained can be suppressed to 370 Bq/g of solid or less. Thereby, the sheet is out of the application range of the Radiation Hazards Prevention Law, restriction at treatment is mitigated and there is little fear that radiation hazard is generated.

The radioactive powders 20 are obtained by pulverizing ores containing natural radioactive substance such as monazite as previously mentioned, and it is preferable to pulverize the particle diameter of from # 46 (420 µm) to # 220 (44 µm) in like manner as the photocatalyst powder 10, considering that the powder used by being supported on the carrier 30 such as nonwoven fabric as previously mentioned.

When the functional sheet 1 of the present invention which is composed above is worn on the body, effects such as analgesic effect, prevention of etiology, renovation of gene, removal of abnormal cell, activation of immune system and hormone system, and rejuvenation of cell membrane, are obtained by the minute dose of radiation ray radiated by the radioactive powder 20 supported on the nonwoven fabric, and the photocatalyst powder 10 supported on the nonwoven fabric together with the radioactive powder 20 exercises a photocatalyst function in response to radiation ray (γ-rays) of which the radioactive powder 20 generates and exercises various effects such as generation of minus ions, promotion of blood circulation, and decomposition of harmful substances and deodorization.

Thus, in the functional sheet 1 of the present invention, even if the content of a radioactive substance is comparatively a little amount out of the application range of the Radiation Hazards Prevention Law, the photocatalyst function which the photocatalyst powder 10 exercises supplements the healing effect of radiation ray, and radiation ray of which the radioactive powder 20 radiates acts as electromagnetic wave which induces the photocatalyst function of the photocatalyst powder 10, and both powders complement functions each other and the sheets exercise healing effect with high efficiency, and other functions.

EMBODIMENTS

Then, the performance test of the functional sheet 1 of the present invention is explained below.

Test Example 1

Confirmation Test of Promotion Effect of Blood Circulation (1) Test Method

Each of a functional sheet 1 of Embodiment 1 and functional sheets 1' and 1" of Comparative Examples 1 and 2 which are described below were wound on the wrist of a test subject (48 years old, male), and tests of comparing by thermography body heat from the arm to the fingertip in the lapse of 30 minutes after wearing were carried out.

The compositions of the respective functional sheets 1, 1' and 1" of Embodiment 1, Comparative Examples 1 and 2 which were used in the above-mentioned comparative tests were as the underdescription.

(2) Structure of Functional Sheet

Figure 4:
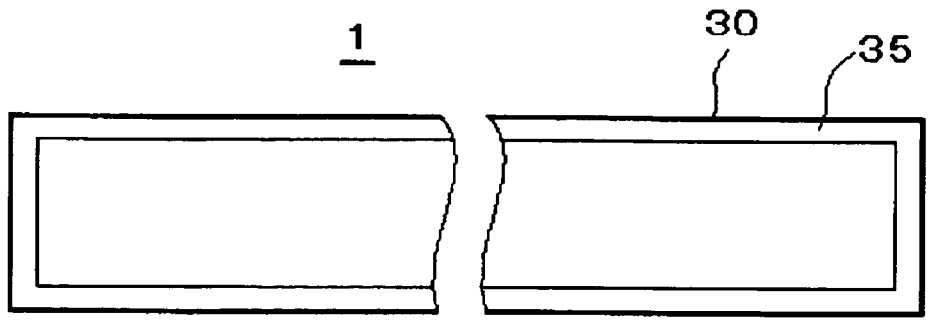
FIG. 4 is a plan view of a functional sheet of Embodiment 1.

1) Embodiment 1 a. Composition member (1) Carrier (Nonwoven Fabric)
Material: Polyester
Size: 250×30 mm, thickness of about 0.5 mm
Amount used: 4 Sheets
(2) Photocatalyst Powder
Material: Titanium oxide
Particle diameter: 150 μm
Amount used: 3 g
Preparation method: Titanium oxide powder was produced by injecting powder of titanium at injection pressure of 0.6 MPa (injection speed of 200 m/sec) and bombarding the powder on a collision substance (material: titanium). In order to form an oxide layer having oxygen deficit tilting structure, it is presumed that titanium oxide of rutile type and anatase type is mixed in titanium oxide used in the present embodiment.
(3) Radioactive Powder
Material: Powder of monazite
Component and concentration by weight: O (43.79%), Al (3.31%), Si (1.73%), P (11.49%), Fe (3.60%), Sn (0.91%), La (10.16%), Ce (21.07%), Th (3.95%)
Particle diameter: 210 μm
Amount used: 1.5 g b. Structure As shown in FIG. 3, four sheets of nonwoven fabrics 31 to 34 were overlapped or laminated, 3 g of the photocatalyst powder 10 (powder of titanium oxide) was respectively placed between the first and the second layers 31 and 32 and between the third and the fourth layers 33 and 34, 1.5 g of the radioactive powder 20 (powder of monazite) was placed between the second and the third layers 32 and 33, and as shown in FIG. 4, the four sheets were sealed by setting a peripheral rim of 4 mm as a seal portion 35.

2) Comparative Example 1

Figure 5:
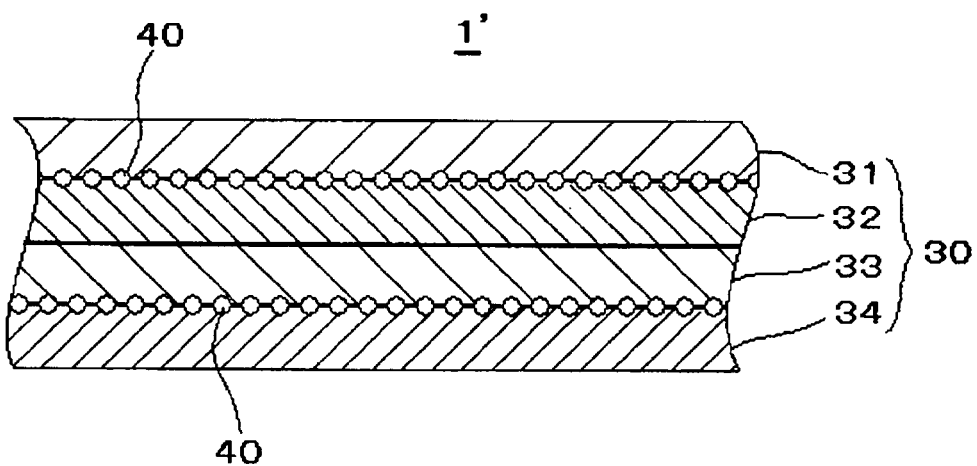
FIG. 5 is a sectional schematic view of a functional sheet of Comparative Example 1.

As shown in FIG. 5, four sheets of nonwoven fabrics 31 to 34 were overlapped or laminated, 1.5 g of the powder 40 of tourmaline which was pulverized at a particle diameter of 210 μm was respectively placed between the first and the second layers 31 and 32 and between the third and the fourth layers 33 and 34, nothing was placed between the second and the third layers 32 and 33, and the four sheets were sealed by setting a peripheral rim of 4 mm as a seal portion 35.

A nonwoven fabric used was the same as Embodiment 1.

3) Comparative Example 2

Figure 6:
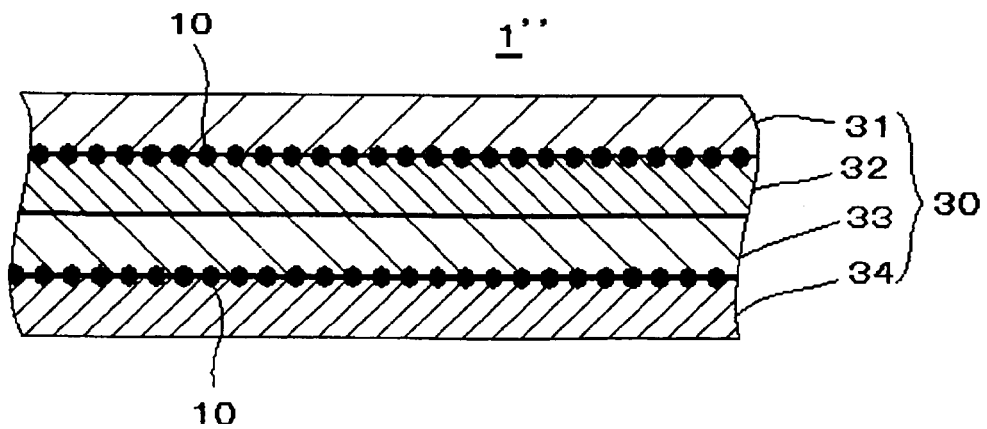
FIG. 6 is a sectional schematic view of a functional sheet of Comparative Example 2.

The structure was the same as that of Embodiment 1 except that the powder of monazite was not placed between the second and the third layers 32 and 33 (refer to FIG. 6).

(3) Test Result

As the result of above comparison, it could be confirmed that when the functional sheet 1 of Embodiment 1 was wound on the wrist, body heat was most raised. Further, although it was also confirmed that, with respect to Comparative Examples, body heat was raised for Comparative Example 2 and Comparative Example 1 following Embodiment 1, in order, either was low in the level of the raise in comparison with Embodiment 1.

In particular, with respect to the functional sheet 1' of Comparative Example 1 in which the powder of tourmaline was supported, body heat was low yet for the portion of the fingertip which was separated from the wrist being a mounting position, and to the contrary, when the functional sheet 1 of Embodiment 1 was worn, it could be confirmed that body heat was wholly raised not only nearby the wrist at a wearing position, but from the arm to the fingertip.

Further, compared with the functional sheet 1" of Comparative Example 2 in which the powder of monazite was not supported, it could be confirmed that the raise range of body heat was remarkably spread for the functional sheet 1 of Embodiment 1.

From these test results, it is considered that the photocatalyst function of the photocatalyst powder is promoted by radiation ray (γ-rays) which are radiated by monazite and the promotion effect of blood circulation is enhanced by synergic effect with radiation ray.

Further, it can be confirmed from the above-mentioned test results that the functional sheet 1 of Embodiment 1 has extremely superior promotion effect of blood circulation and it is considered that when the functional sheet is used by being pasted on the body, there is effect for curing of stiff neck and feeling of cold.

Test Example 2

Measurement Test of Dose of Radiation Ray

4) Example 2

Two Sheets of nonwoven fabrics were stitched in a condition in which 4 g of the powder of titanium oxide and 2.0 g of the powder of monazite were placed in a mixed condition between 2 sheets of nonwoven fabrics of 100×100 mm, to produce a functional sheet with a total weight of 6.4 g.

Further, the respective compositions of the material of the nonwoven fabric, titanium oxide being the photocatalyst powder and the powder of monazite being the radioactive powder were similar as Embodiment 1.

(1) Measurement Method

The values of γ-ray when distances from the functional sheet were set as 0 mm, 10 mm, 20 mm, 30 mm and 50 mm and the values (background) of γ-ray when the functional sheet did not exist were measured by a radiation counter.

(2) Measurement Result

Measurement result above is shown in the undermentioned Table 1.

[Table 1]

TABLE 1

Distance from nonwoven fabric and γ-ray value

| Distance (mm) | γ-ray value (μ Sv/h) |
|---|---|
| Background | 0.056 |
| 0 | 0.180 |
| 10 | 0.142 |
| 20 | 0.121 |
| 30 | 0.089 |
| 50 | 0.070 |

(3) Evaluation (Evaluation of Safety)

From the above-mentioned measurement result, since the dose (background) of γ-ray in the natural world was 0.056 μSv/h, and since the dose of radiation ray of the nonwoven fabric of the functional sheet used in the above-mentioned test was an average of 0.180 μSv/h (0.200 μSv/h at maximum) at a distance of 0 mm, it could be confirmed that γ-rays generated could be suppressed to a trace dose of radiation ray, which was about 3-fold of the natural world, in the fore-mentioned example in which the content of monazite in the functional sheet with the total weight of 6.4 g was 2.0 g (in the present embodiment which used monazite having a thorium content of 3.95 wt %, the thorium content for the total weight was about 1.23 wt % which was within a range of 0.1 to 2.0 wt % of the present application).

Further, considering the exposed dose which is increased by mounting the functional sheet assuming that the above-mentioned functional sheet is directly brought in contact with the body (a distance of 0 mm), the exposed dose per one hour which is increased by wearing the sheet is 0.180 μSv/h−0.056 μSv/h=0.124 μSv/h.

When a person is exposed for one year (365 days×24 hours=8760 hours) at this exposed dose of γ-rays, the total of the exposed dose is 0.124 μSv/h×8760 h≈1086 μSv/year=1.086 mSv/year, and is about the same value as the dose limit (general public: 1 mSv/year) based on the recommendation which was published in 1977 by ICRP (International Commission on Radiological Protection).

Further, since the functional sheet is removed from the body at bathing and the like, the increased dose of the exposed dose during one year (365 days×22 hours=8030 hours) is 0.124 μSv/h×8030 h≈996 μSv/year=0.996 mSv/year, assuming that there is a time of 2 hours on average per day in which the functional sheet is not worn, thus the increased dose is less than the dose limit.

It can be confirmed from the points above that the functional sheet of the present application has no problem in safety at use.

INDUSTRIAL APPLICABILITY

The functional sheet of the present invention is not limited to the uses in the fore-mentioned examples, and can be applied to various products as a sheet shape as it is, or by carrying out a secondary process to the sheet of cutting, stitching, adhesion, and the like into a predetermined shape. And aiming to various effects by generation of radiation ray and/or minus ions including healing effect, promotion of blood circulation, relaxation, antibacterial effect, deodorization, and the like, in addition to a healing tool which is used by being pasted on the body as previously described and the like, the functional sheet of the present invention can be utilized for clothes such as an underwear, a cap, gloves, socks and an eye mask, for ornaments such as a necklace, a choker (collar) and a bracelet, for bed clothes such as a sheet and a quilt cover, for interior appliance article such as a curtain, a table cloth and a carpet, and for joinery such as a wall paper and a sliding screen.

Further, the functional sheet of the present invention can be also widely used for fields which require antibacterial, deodorization effect, and the like, including, a filter for air conditioner, air cleaner, cleaner, range hood, and the like, sanitary goods such as a mask, antifouling sheets for a pet and the like. So the application field of the functional sheet of the present invention is wide.

Thus, the broadest claims that follow are not directed to a machine that is configuration a specific way. Instead, said broadest claims are intended to protect the heart or essence of this breakthrough invention. This invention is clearly new and useful. Moreover, it was not obvious to those of ordinary skill in the art at the time it was made, in view of the prior art when considered as a whole.

Moreover, in view of the revolutionary nature of this invention, it is clearly a pioneering invention. As such, the claims that follow are entitled to very broad interpretation as to protect the heart of this invention, as a matter of law.

It will thus be seen that the objects set forth above, and those made apparent from the foregoing description, are efficiently attained. Also, since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described;

What is claimed is:

1. A functional sheet comprising:

a photocatalyst powder in which a metal powder exercising a photocatalyst function by oxidation is oxidized, said photocatalyst powder having a structure of which a bond with oxygen is decreased as it goes from the surface of the powder to the inside gradually;

a radioactive powder containing a natural radioactive substance;

a carrier formed in a sheet shape composed by entangling a lot of fibers to a level at which air permeability can be secured, said fibers entangled with permeability sufficient to pass air but not to pass said photocatalyst powder and said radioactive powder said carrier having a laminated structure to and supporting said photocatalyst powder and said radioactive powder by placing the powders between the laminated structure of said carrier in a condition in which the powders are mutually brought in contact or adjacent; and said photocatalyst powder being obtained by injecting and bombarding said metal powder on an object to be bombarded comprising metal, ceramics, or a mixture thereof which has a melting point equal or more to a melting point of the metal powder, together with compressed gas.

2. The functional sheet according to claim 1, wherein the photocatalyst powder and the radioactive powder are supported by placing the powders between the laminated structure of the carrier in a mixed condition.

3. The functional sheet according to claim 1, wherein the carrier has the laminated structure of 3 layers or more and the photocatalyst powder and the radioactive powder are supported by placing the photocatalyst powder and the radioactive powder respectively between the laminated structure layers of the carrier individually.

4. The functional sheet according to any one of claim 1, wherein the photocatalyst powder and the radioactive powder having a particle diameter of from # 46 (420 mm) to # 220 (44 mm).

5. The functional sheet according to any one of claim 1, wherein the natural radioactive substance is thorium and the radioactive powder is supported so that thorium is 0.1 to 2.0 wt % at a weight ratio based on the total weight of the functional sheet obtained.

* * * * *